(12) United States Patent
Ishiwata

(10) Patent No.: US 10,285,796 B2
(45) Date of Patent: May 14, 2019

(54) PROSTHESIS PACKAGING CASE, PROSTHESIS, AND PROSTHESIS WITH PACKAGING CASE

(71) Applicant: NANTOH. CO., LTD, Numazu-shi, Shizuoka (JP)

(72) Inventor: Teruo Ishiwata, Numazu (JP)

(73) Assignee: NANTOH. CO., LTD, Numazu-shi (JP)

(*) Notice: Subject to any disclaimer, the term of this patent is extended or adjusted under 35 U.S.C. 154(b) by 0 days.

(21) Appl. No.: 15/579,297

(22) PCT Filed: Jul. 1, 2015

(86) PCT No.: PCT/JP2015/068951
§ 371 (c)(1),
(2) Date: Dec. 4, 2017

(87) PCT Pub. No.: WO2017/002224
PCT Pub. Date: Jan. 5, 2017

(65) Prior Publication Data
US 2018/0296314 A1    Oct. 18, 2018

(51) Int. Cl.
*A61C 8/00* (2006.01)
*A61F 2/00* (2006.01)
(Continued)

(52) U.S. Cl.
CPC ............... *A61F 2/0095* (2013.01); *A61C 8/00* (2013.01); *A61C 8/0087* (2013.01); *A61C 19/02* (2013.01);
(Continued)

(58) Field of Classification Search
CPC . A61F 2/0095; A61F 2/28; A61F 2/30; A61C 8/0087; A61C 19/02; A61L 2/081;
(Continued)

(56) References Cited

U.S. PATENT DOCUMENTS 5,062,800 A * 11/1991 Niznick ............... A61C 8/0087
206/368
6,247,932 B1   6/2001 Sutter
(Continued)

FOREIGN PATENT DOCUMENTS

JP    2000-512194 A    9/2000
JP    2008-50247 A    3/2008
(Continued)

OTHER PUBLICATIONS

Notification of Reasons for Refusal dated Aug. 3, 2016, issued in counterpart Japanese Patent Application No. 2016-501903, w/English translation (7 pages).
(Continued)

*Primary Examiner* — Nicholas D Lucchesi
(74) *Attorney, Agent, or Firm* — Westerman, Hattori, Daniels & Adrian, LLP

(57) ABSTRACT

A prosthesis-packaging case (20) comprises a primary packaging case (30) for housing a prosthesis (10) and a secondary packaging case (40) for housing the primary packaging case (30), wherein the prosthesis (10) and the primary packaging case (30) are respectively made of a material containing zirconia, the secondary packaging case (40) is made of a heat-resistant material, and the prosthesis (10) is subjected to γ-ray sterilization treatment and heat treatment while double-packaged with the primary packaging case (30) and secondary packaging case (40) to change a color of the prosthesis (10) to a color approximate to that of a natural bone.

15 Claims, 14 Drawing Sheets

(51) Int. Cl.
*A61F 2/28* (2006.01)
*A61F 2/30* (2006.01)
*A61C 19/02* (2006.01)
*A61L 2/08* (2006.01)
*A61L 2/26* (2006.01)
*A61C 13/08* (2006.01)
*A61F 2/32* (2006.01)
*A61C 5/77* (2017.01)

(52) U.S. Cl.
CPC ............... *A61F 2/28* (2013.01); *A61F 2/30* (2013.01); *A61L 2/081* (2013.01); *A61L 2/26* (2013.01); *A61C 5/77* (2017.02); *A61C 13/082* (2013.01); *A61C 2202/00* (2013.01); *A61F 2/2875* (2013.01); *A61F 2/32* (2013.01); *A61L 2202/182* (2013.01); *A61L 2202/21* (2013.01)

(58) Field of Classification Search
CPC ... A61L 2/26; A61L 2202/182; A61L 2202/21
See application file for complete search history.

(56) References Cited

U.S. PATENT DOCUMENTS

| | | | | |
|---|---|---|---|---|
| 6,561,805 B2* | 5/2003 | Kumar | ............... | A61C 8/008 206/368 |
| 6,913,465 B2* | 7/2005 | Howlett | ............... | A61C 8/0087 206/63.5 |
| 7,451,870 B2* | 11/2008 | Donahoe | ............... | A61C 8/0087 206/369 |
| 7,854,316 B2* | 12/2010 | Park | ............... | A61C 8/0087 206/369 |
| 8,070,491 B2* | 12/2011 | Mundwiler | ............... | A61C 8/0089 206/63.5 |
| 8,181,773 B2* | 5/2012 | Guenter | ............... | A61C 8/0087 206/368 |
| 2008/0257760 A1 | 10/2008 | Hanada et al. | | |
| 2010/0003630 A1 | 1/2010 | Yamashita et al. | | |
| 2010/0074789 A1 | 3/2010 | Heuer et al. | | |
| 2011/0056851 A1 | 3/2011 | Schlottig et al. | | |
| 2014/0174971 A1 | 6/2014 | Lindner et al. | | |
| 2016/0022391 A1 | 1/2016 | Ishiwata | | |

FOREIGN PATENT DOCUMENTS

| | | |
|---|---|---|
| JP | 2008-264294 A | 11/2008 |
| JP | 2011-521758 A | 7/2011 |
| JP | 2013-500093 A | 1/2013 |
| JP | 3188325 U | 1/2014 |
| JP | 2015-39422 A | 3/2015 |
| WO | 2011/012287 A1 | 2/2011 |

OTHER PUBLICATIONS

Decision to Grant a Patent dated Dec. 8, 2016, issued in counterpart Japanese Patent Application No. 2016-501903, wlEnglish translation (6 pages).

International Search Report dated Oct. 6, 2015, issued in counterpart International Application No. PCT/JP2015/068951 (2 pages).

* cited by examiner

PROSTHESIS PACKAGING CASE, PROSTHESIS, AND PROSTHESIS WITH PACKAGING CASE

TECHNICAL FIELD

The present invention relates to a packaging case; for example, a packaging case housing a fixture of a dental implant that is embedded into the jaw bone when a tooth root of a permanent tooth is lost.

BACKGROUND ART

A prosthesis is an artifact for supplementing morphology and function of a defective portion in a body.

In dentistry, the prosthesis includes a denture, a crown, a bridge, a dental implant and the like. In surgery, it includes an artificial bone, an artificial organ, an artificial joint implant and the like. In cosmetic surgery, it includes a silicone bag, a silicone resin plate and the like. An artificial eye, an artificial ear and an artificial limb are also included in the prosthesis.

A prosthesis to be embedded in the body may be called prosthesis, and a prosthesis to be attached to the surface of the body may be called epithese.

Implants that are embedded into the body are particularly attracting attention.

For example, the dental implant is inserted into and fixed to a hole provided at the alveolar bone in a case where a tooth root of a permanent tooth has been lost due to dental caries or damage.

This dental implant is composed of a fixture (artificial tooth root) to be fixed to the alveolar bone and an abutment (support base) to be screwed to the fixture. An implant crown (artificial crown) is mounted on the abutment.

The dental implant (fixtures, abutment) is formed of metals such as titanium and titanium alloys, as well as ceramics such as alumina and zirconia. In order to avoid a risk of metal allergy, the dental implant is preferably formed of ceramics.

Since the implant is embedded in the body, sterilization (disinfection) treatment is required. The sterilization treatment for the implant may include gas sterilization with ethylene oxide gas and γ-ray sterilization treatment by γ-ray irradiation.

The sterilization with ethylene oxide gas takes 2 to 4 hours, and furthermore aeration after sterilization takes 8 to 12 hours or longer. In addition, ethylene oxide gas has high toxicity and flammability, and requires careful handling. Gas sterilization with ethylene oxide gas has extremely low work efficiency and is also difficult to handle.

On the other hand, the γ-ray sterilization treatment is superior in that the treatment time is short and there is no risk of residual gas or the like.

For the implant formed of zirconia, the γ-ray sterilization treatment has not been adopted. This is because zirconia becomes dark brown by the γ-ray sterilization treatment, and aesthetics is compromised.

However, a technique of whitening by heating a dark-browned zirconia has been developed (Patent Document 1). This technique allowed the γ-ray sterilization treatment to be adopted even when the implant was formed of zirconia.

PRIOR ART DOCUMENTS

Patent Documents

Patent Literature 1: Japanese Patent Application Laid-Open No. 2015-039422

SUMMARY OF INVENTION

Problem to be Solved

However, there was a problem that a packaging case capable of properly sealing an implant whitened by the technique of Patent Literature 1 had not been developed.

Since the packaging case is subjected to γ-ray sterilization treatment and heat treatment while housing a zirconia implant, properties such as radiation resistance and heat resistance are required. In addition, since it is necessary to maintain the sterilized state of the implant for a long period, properties such as non dust-generating property, durability and stability are required.

In order to avoid the risk of metal allergy, it is desirable to use materials other than metals also for the packaging case.

It is an object of the present invention to provide a prosthesis-packaging case which can be subjected to γ-ray sterilization treatment and heat treatment while housing a zirconia prosthesis and can thereafter maintain a sterilized state for a long period, as well as a prosthesis, and a prosthesis with the packaging case.

Solution to Problem

According to the first embodiment of a prosthesis-packaging case of the present invention, the prosthesis-packaging case comprises a primary packaging case for housing a prosthesis and a secondary packaging case for housing the primary packaging case, wherein the prosthesis and the primary packaging case are respectively made of a material containing zirconia, the secondary packaging case is made of a heat-resistant material, and the prosthesis is subjected to γ-ray sterilization treatment and heat treatment while double-packaged with the primary and secondary packaging cases to change a color of the prosthesis to a color approximate to that of a natural bone.

According to the second embodiment of the prosthesis-packaging case of the present invention, in the first embodiment, the color approximate to that of the natural bone has an L* value of 60 to 90, an a* value of −5 to 10, and a b* value of −5 to 10 in the L*a*b* color space.

According to the third embodiment of the prosthesis-packaging case of the present invention, in the first or the second embodiment, the heat treatment has a highest temperature of 100° C. to 300° C.

According to the fourth embodiment of the prosthesis-packaging case of the present invention, in any one of the first to the third embodiments, the primary packaging case comprises a primary case body for housing the prosthesis, a primary lid fitted into the primary case body, and a primary sealing body disposed between the primary case body and the primary lid. The primary case body may be a jar or a bottle.

According to the fifth embodiment of the prosthesis-packaging case of the present invention, in any one of the first to the fourth embodiments, the secondary packaging case comprises a secondary case body for housing the primary packaging case, a secondary lid screwed to the secondary case body, and a secondary sealing body disposed between the secondary case body and the secondary lid. The secondary case body may be a jar or a bottle.

According to the sixth embodiment of the prosthesis-packaging case of the present invention, in any one of the first to the fifth embodiments, the secondary packaging case is made of a thermoplastic resin.

According to the seventh embodiment of the prosthesis-packaging case of the present invention, in any one of the first to the sixth embodiments, the prosthesis is an implant embedded in a body.

According to the eighth embodiment of the prosthesis-packaging case of the present invention, in the seventh embodiment, the prosthesis is a dental implant.

According to the ninth embodiment of the prosthesis-packaging case of the present invention, in the seventh embodiment, the prosthesis is an artificial joint implant.

According to the tenth embodiment of the prosthesis-packaging case of the present invention, in the seventh embodiment, the prosthesis is an artificial bone or a bone prosthetic material.

An embodiment of a prosthesis of the present invention is a prosthesis made of a material containing zirconia and subjected to γ-ray sterilization treatment and heat treatment to change a color of the prosthesis to a color approximate to that of a natural bone, wherein the prosthesis is subjected to the γ-ray sterilization treatment and the heat treatment while double-packaged with a primary packaging case made of a material containing zirconia and a secondary packaging case made of a heat-resistant material.

An embodiment of a prosthesis with a packaging case of the present invention comprises a prosthesis, a primary packaging case for housing the prosthesis, and a secondary packaging case for housing the primary packaging case, wherein the prosthesis and the primary packaging case are respectively made of the material containing zirconia, the secondary packaging case is made of the heat-resistant material, and the prosthesis is subjected to γ-ray sterilization treatment and heat treatment while double-packaged with the primary packaging case and the secondary packaging case to change a color of the prosthesis to a color approximate to that of a natural bone.

Effects of Invention

The prosthesis-packaging case of the present invention can be subjected to the γ-ray sterilization treatment and the heat treatment while housing the prosthesis containing zirconia. Furthermore, the sterilized state of the prosthesis colored to a color approximate to that of the natural bone can be maintained for a long period.

The prosthesis and the prosthesis with the packaging case of the present invention are colored to a color approximate to that of the natural bone. Since no coloring material is used, there is no adverse effect on the human body.

The prosthesis and the prosthesis with the packaging case are subjected to the γ-ray sterilization treatment and the heat treatment while housed in the prosthesis-packaging case, and stored and transported as they are. Thus, the sterilized state can be maintained for a long period. In particular, since the prosthesis-packaging case is made of the same material as of the prosthesis, foreign matters do not adhere to the prosthesis.

DESCRIPTION OF EMBODIMENTS

The embodiments of the present invention will be described with reference to drawings. Various sizes and the like shown in the following description are only examples.

[Dental Implant 5]

Figure 1:
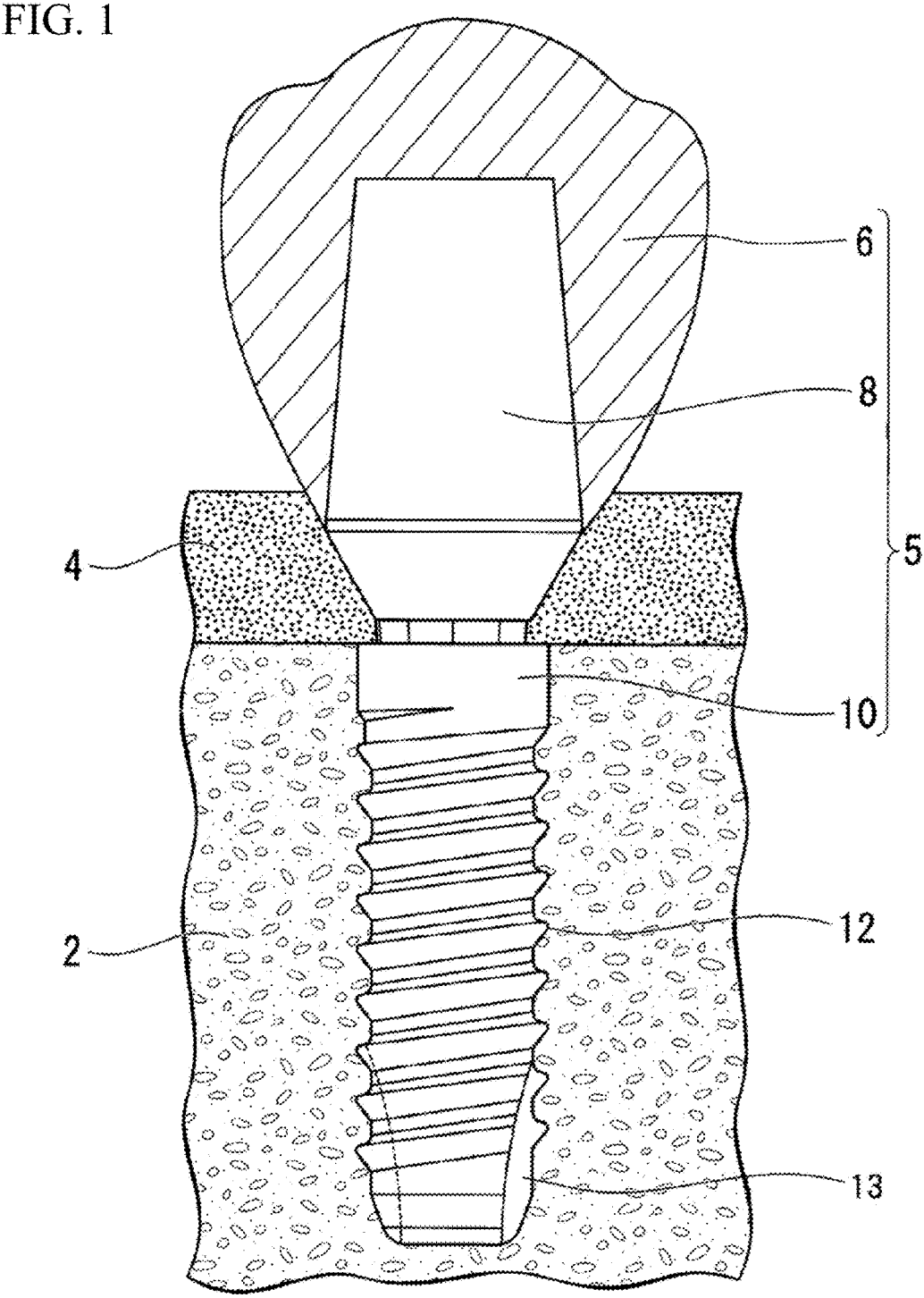
FIG. 1 is a diagram showing a dental implant 5 according to the embodiment of the present invention.

FIG. 1 is a diagram showing a dental implant 5 according to the embodiment of the present invention.

A dental implant (prosthesis, implant, prosthesis with packaging case) 5 is fixed to an alveolar bone 2.

The dental implant 5 includes a fixture 10 to be fixed to an alveolar bone 2, an abutment body 8 that is fitted in the fixture 10.

A male screw 12 is formed on the outer peripheral surface of the fixture 10. In addition, a self tap 13 is formed on the tip side of the male screw 12. By screwing the male screw 12 into a hole formed in an alveolar bone 2, the fixture 10 is fixed to the alveolar bone 2.

An implant crown 6 is attached to the outer peripheral surface of the abutment (prosthesis, implant, prosthesis with packaging case) 8 by using an adhesive or the like. The implant crown 6 is also called an upper structure or an artificial crown.

A base end side beyond the implant crown 6 is covered with a gum 4.

The abutment 8 and the fixture 10 are formed of ceramics containing zirconia as a main component. The implant crown (prosthesis, implant, prosthesis with packaging case) 6 may also be formed of zirconia.

As described later, the fixture 10 and the like are subjected to γ-ray sterilization treatment and heat treatment. In particular, since the fixture 10 is embedded in a body (alveolar bone 2), sterilization treatment is indispensable for preventing infection.

[Packaging Case 20]

Figure 2:
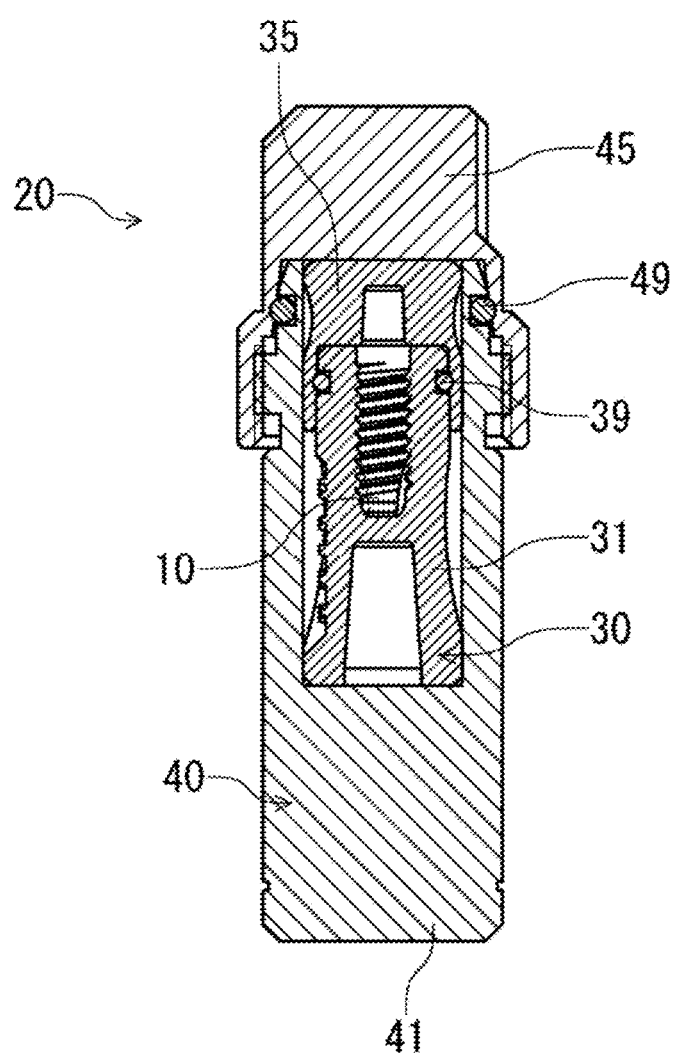
FIG. 2 is a sectional view showing a packaging case 20 according to the embodiment of the present invention.

FIG. 2 is a sectional view showing the packaging case 20 according to the embodiment of the invention.

Figure 3:
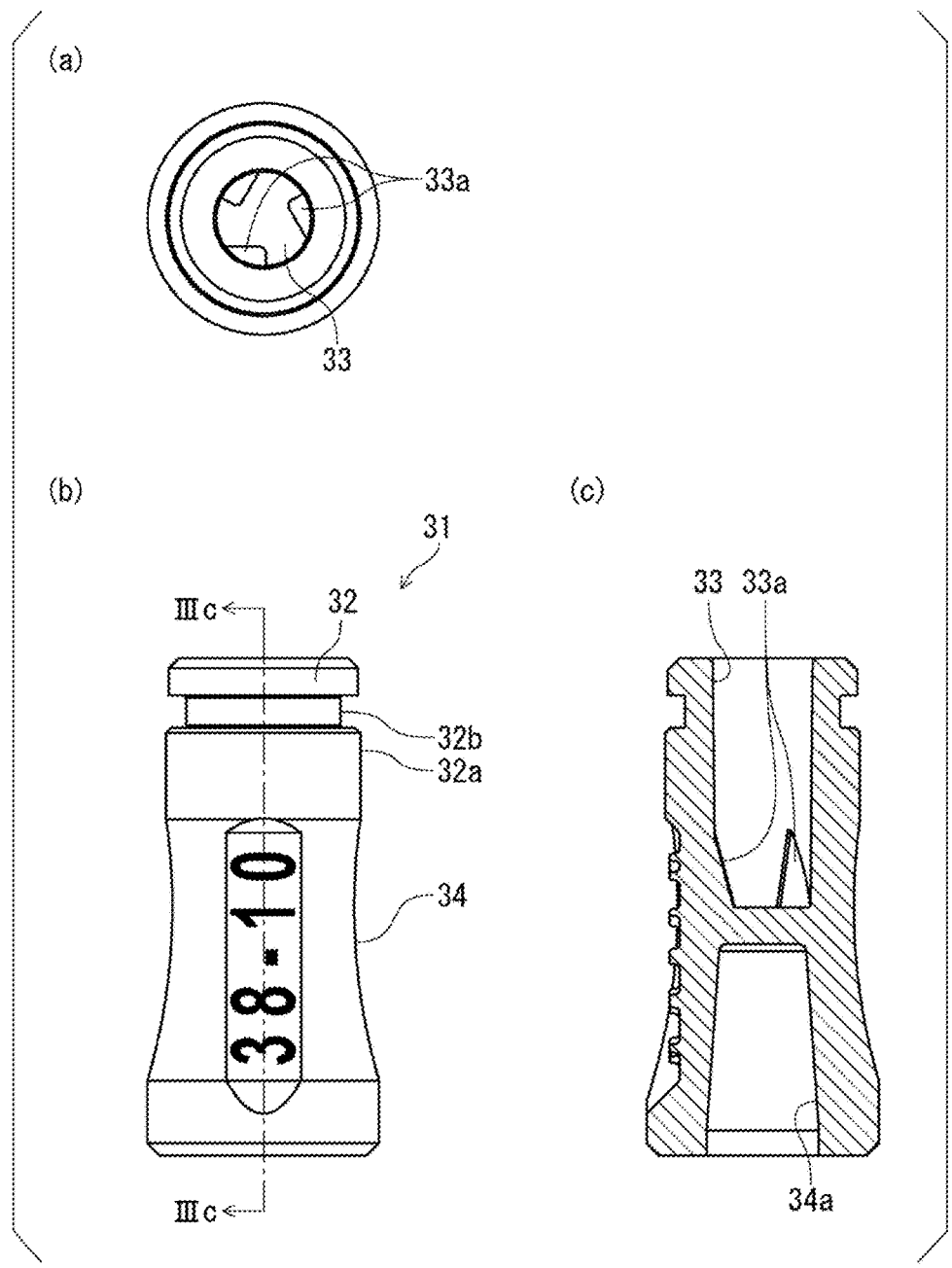
FIG. 3 is (a) plan view, (b) front view and (c) IIIc-IIIc sectional view of a primary jar 31 of a primary packaging case 30 according to the embodiment of the present invention.

FIG. 3 is (a) plan view, (b) front view and (c) IIIc-IIIc sectional view of a primary jar 31 of a primary packaging case 30 according to the embodiment of the present invention.

Figure 4:
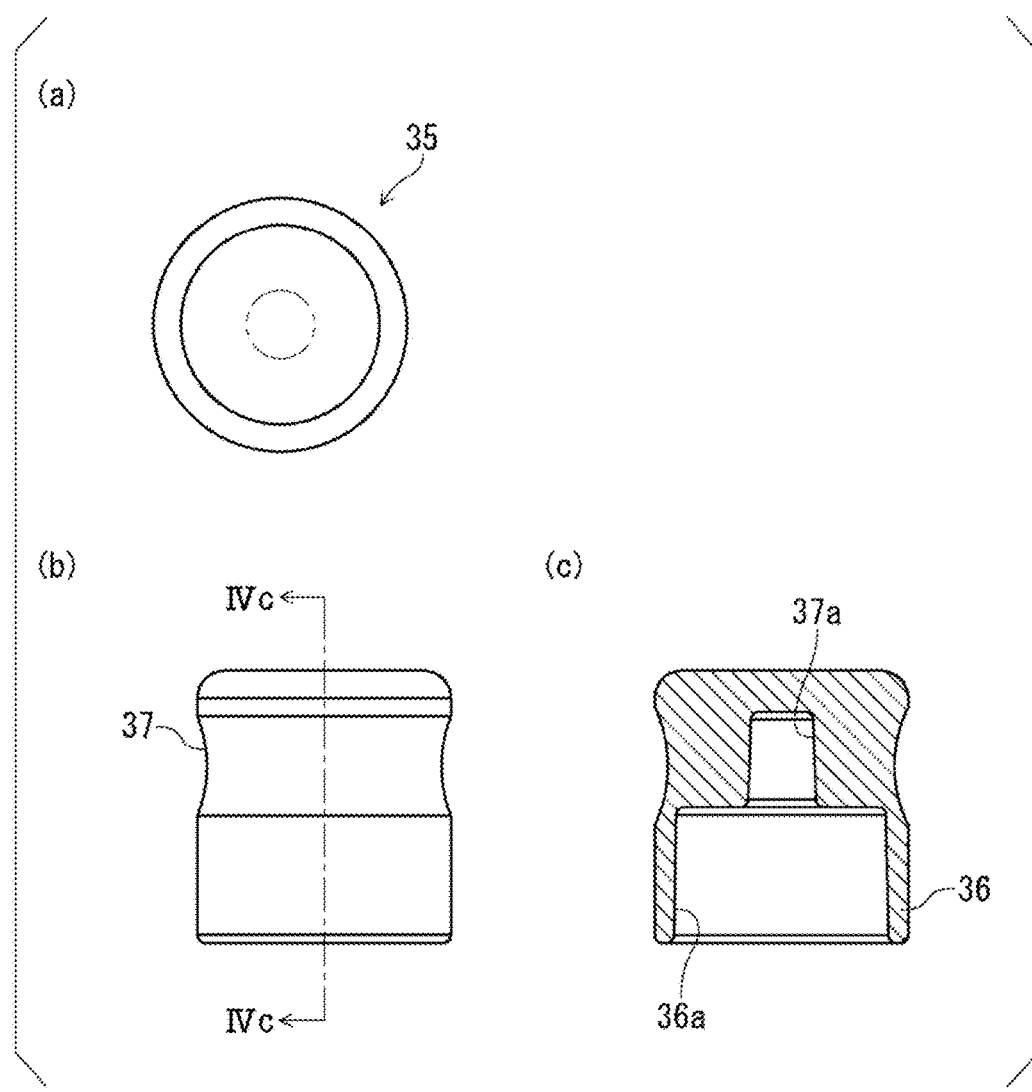
FIG. 4 is (a) plan view, (b) front view and (c) IVc-IVc sectional view of a primary cap 35 of the primary packaging case 30 according to the embodiment of the present invention.

FIG. 4 is (a) plan view, (b) front view and (c) IVc-IVc sectional view of a primary cap 35 of the primary packaging case 30 according to the embodiment of the present invention.

Figure 5:
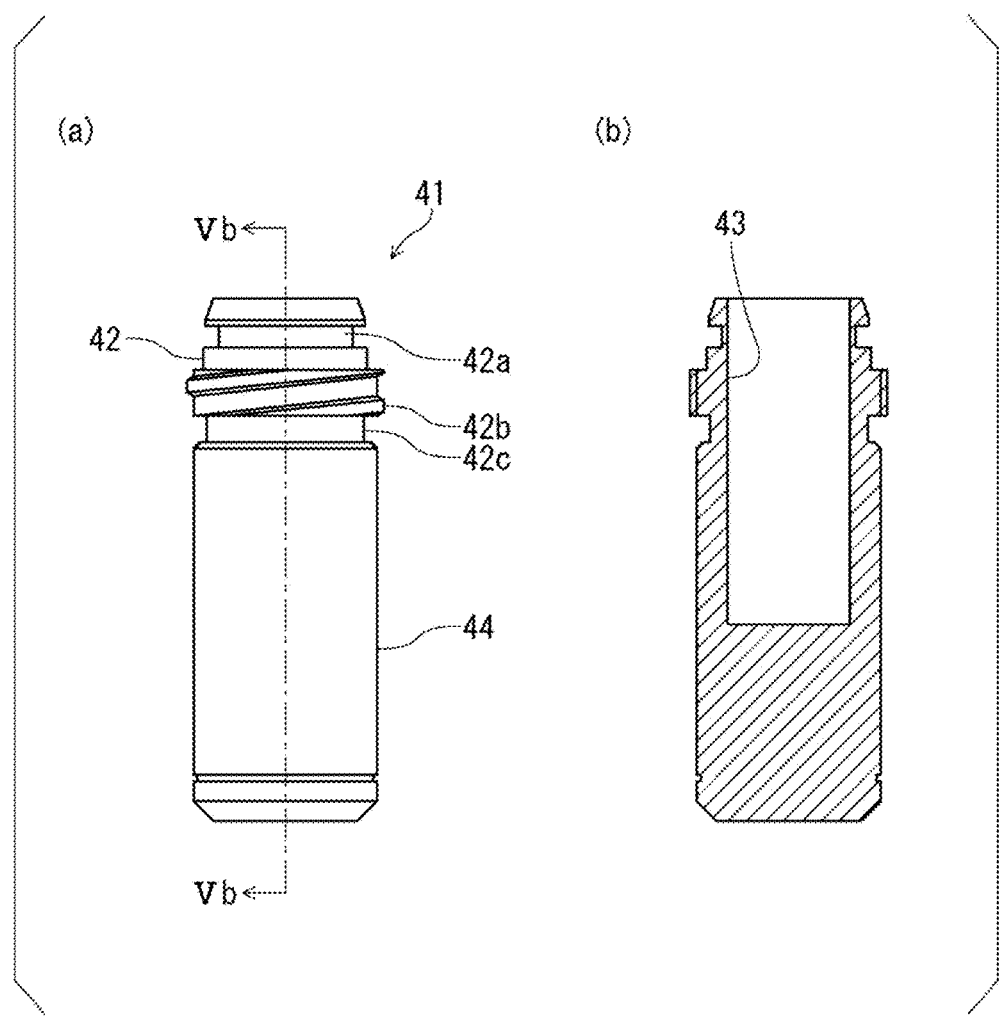
FIG. 5 is (a) front view and (b) Vb-Vb sectional view of a secondary jar 41 of a secondary packaging case 40 according to the embodiment of the present invention.

FIG. 5 is (a) front view and (b) Vb-Vb sectional view of a secondary jar 41 of a secondary packaging case 40 according to the embodiment of the invention.

Figure 6:
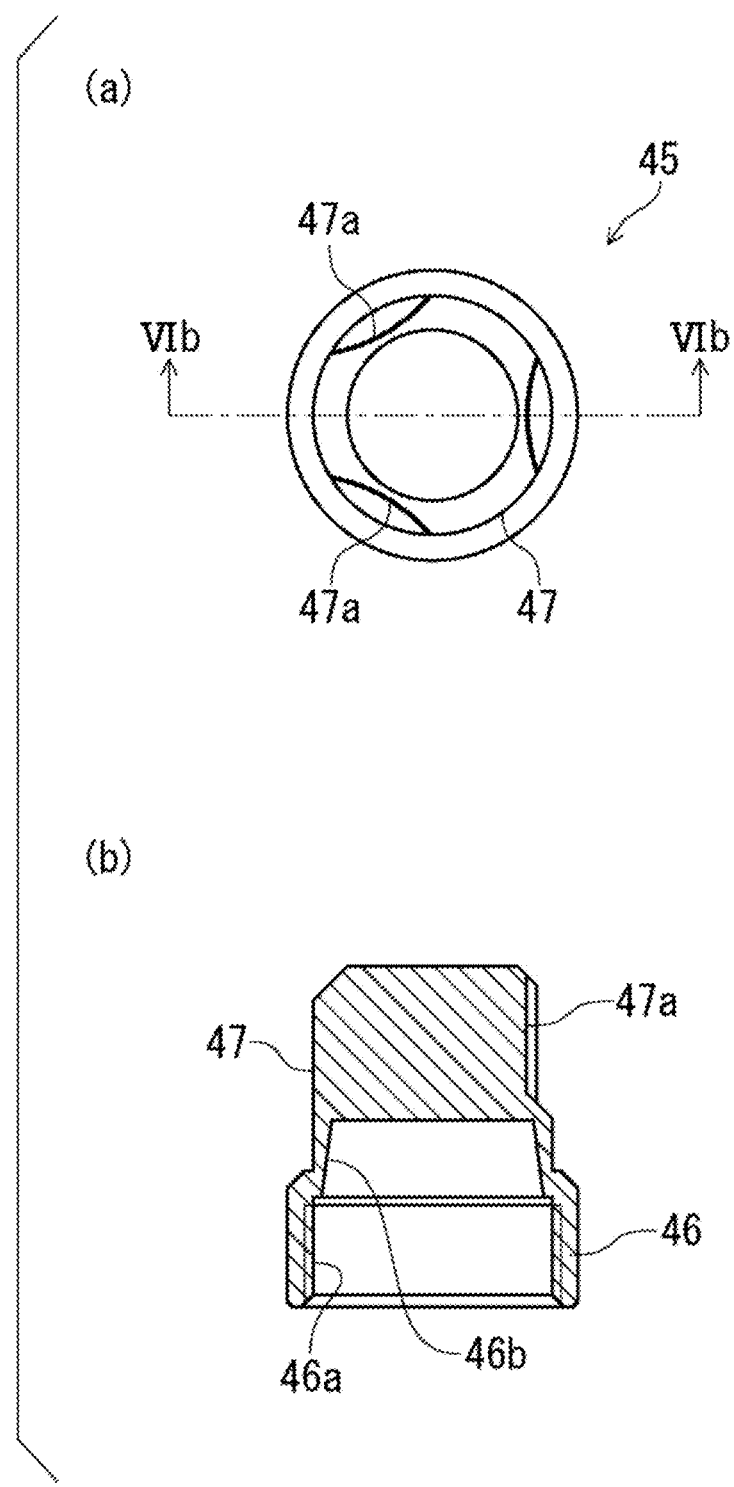
FIG. 6 is (a) front view and (b) VIb-VIb sectional view of a secondary cap 45 of the secondary packaging case 40 according to the embodiment of the present invention.

FIG. 6 is (a) front view and (b) VIb-VIb sectional view of a secondary cap 45 of the secondary packaging case 40 according to the embodiment of the invention.

In order to maintain the sterilized state, the fixture 10 is sealed in the packaging case 20 until just before use. The packaging case (prosthesis-packaging case) 20 comprises a primary packaging case 30 and a secondary packaging case 40, so that the fixture 10 is double-packaged.

The primary packaging case 30 directly houses the fixture 10 to properly protect the fixture 10 during transportation and storage while preventing bacterial invasion. The secondary packaging case 40 houses the primary packaging case 30 to appropriately protect the fixture 10 during transportation and storage.

[Primary Packaging Case 30]

The primary packaging case 30 comprises the primary jar 31, the primary cap 35 and a primary O-ring 39, and the primary cap 35 is fitted into a mouth portion 32 of the primary jar 31 so that they are connected.

The primary O-ring (primary sealing body) 39 is made of a heat-resistant rubber such as a silicone rubber and is disposed between the primary jar 31 and the primary cap 35. Thereby, the inside of the primary packaging case 30 is sealed.

The primary O-ring 39 may be made of not only a silicone rubber but also e.g. a fluororubber such as Teflon (registered trademark).

The primary packaging case 30 (primary jar 31 and primary cap 35) is formed of ceramics comprising zirconia as a main component. That is, the primary packaging case 30 is formed of the same material as the fixture 10.

If the primary packaging case 30 were formed of a material different from that of the fixture 10, impurities (foreign matters: contamination) could adhere to the fixture 10 from the primary packaging case 30.

Thus, the primary packaging case 30 is formed of the same material as the fixture 10, so that the adhesion of the impurities from the primary packaging case 30 to the fixture 10 is avoided. Thereby, the primary packaging case 30 can maintain the sterilized state of the fixture 10 for a long period.

When the primary packaging case 30 (primary jar 31 and primary cap 35) is formed of zirconia, a connecting structure other than screwing is required. This is because, when the primary jar 31 and the primary cap 35 are screwed to each other, both screws (screw opening and screw cap) are burned together (galling), and thus opening becomes difficult.

Thus, in the primary packaging case 30, the primary jar 31 and the primary cap 35 are fitted to each other for connection.

The primary jar 31 is an elongated bottomed cylindrical member and has a wide mouth portion 32.

That is, the primary jar 31 is an elongated wide-mouth case body.

On the outer peripheral surface of the mouth portion 32, a fitting portion 32a having a high circularity is formed. The fitting portion 32a is about one-fourth the total length in the longitudinal direction of the primary jar 31. The primary cap 35 is fitted into the fitting portion 32a.

On a part of the fitting portion 32a, an O-ring groove 32b is formed along the circumferential direction. On this O-ring groove 32b, the primary O-ring 39 is disposed.

The primary jar 31 has a housing portion 33 having substantially the same shape as the outer shape of the fixture 10. The housing portion 33 is excavated from the tip (mouth portion 32) of the primary jar 31 to the middle in the longitudinal direction. The longitudinal length of the housing portion 33 is substantially equal to that of the fixture 10.

A rotation stopper 33a engaging with a self tap 13 of the fixture 10 is formed on the bottom of the housing portion 33. The self tap 13 and the rotation stopper 33a are engaged with each other so that the fixture 10 is housed in the housing portion 33 without being capable of axially rotating.

In the primary jar 31, a gripping portion 34 is formed on the bottom end side beyond the housing portion 33. The gripping portion 34 has a shape that the middle in the longitudinal direction is constricted, and its diameter slightly increases toward the bottom end. This makes it easier to pinch the primary jar 31 with fingers.

The size of the fixture 10 is impressed on a part of the gripping portion 34. The impression "38-10" means that the fixture 10 has a diameter of 3.8 mm and a length of 10 mm.

In the inside of the gripping portion 34, a lightening hole 34a is formed to reduce the weight of the primary jar 31. The lightening hole 34a is excavated from the bottom end of the primary jar 31 to the vicinity of the middle in the longitudinal direction.

The primary cap (primary lid) 35 is a short bottomed cylindrical member and has a cylindrical portion 36 to be fitted into the primary jar 31.

On the inner peripheral surface of the cylindrical portion 36, a fitting portion 36a having a high circularity is formed. The fitting portion 36a is about one-half the total length in the longitudinal direction of the primary cap 35. The fitting portion 36a is fitted into the fitting portion 32a of the primary jar 31. In addition, when the primary cap 35 is fitted into the primary jar 31, the fitting portion 36a is closely attached to the primary O-ring 39.

In the primary cap 35, a gripping portion 37 is also formed on the bottom end side of the cylindrical portion 36. The gripping portion 37 has a shape that the middle in the longitudinal direction is constricted. This makes it easier to pinch the primary cap 35 with fingers.

In the inside of the gripping portion 34, a lightening hole 37a is formed to reduce the weight of the primary cap 35. The lightening hole 37a is excavated from the bottom face of the cylindrical portion 36 to the bottom end of the primary cap 35.

[Secondary Packaging Case 40]

The secondary packaging case 40 comprises the secondary jar 41, the secondary cap 45 and a secondary O-ring 49, and the secondary cap 45 is screwed to a mouth portion 42 of the secondary jar 41 so that they are connected.

Like the primary O-ring 39, the secondary O-ring (secondary sealing body) 49 is made of a heat-resistant rubber such as a silicone rubber and a fluororubber, and is disposed between the secondary jar 41 and the secondary cap 45. The secondary O-ring 49 seals the inside of the secondary packaging case 40.

The secondary packaging case 40 (secondary jar 41 and secondary cap 45) is formed of a heat-resistant material. Specifically, the secondary packaging case 40 is made of a thermoplastic resin such as polyether ether ketone (PEEK).

The secondary packaging case 40 requires durability (flame retardancy, heat resistance) for preventing damage even in heat treatment. Specifically, a performance of preventing damage even when the case is heated at about 200° C. is required.

Thus, the secondary packaging case 40 is made of a heat-resistant resin and subjected to the heat treatment while housing the fixture 10.

In addition, the secondary packaging case 40 requires a structure for preventing it from opening in association with the expansion of the internal air in the heat treatment. This is because the primary jar 31 and the primary cap 35 of the primary packaging case 30 are merely fitted into each other, and thus when the internal air expands due to the heat treatment, the case 30 will open.

Consequently, in the secondary packaging case 40, a structure that the primary jar 31 and the primary cap 35 cannot be moved is adopted. Specifically, in the secondary packaging case 40, the secondary jar 41 and the secondary cap 45 are screwed and connected to each other to house the primary packaging case 30 with no gap.

The secondary jar 41 is an elongated bottomed cylindrical member and has a wide mouth portion 42.

That is, like the primary jar 31, the secondary jar 41 is an elongated wide-mouth case body.

On the outer peripheral surface of the mouth portion 42, an O-ring groove 42a is formed along the circumferential direction on the tip side. Furthermore, on the outer peripheral surface of the mouth portion 42, a screw portion 42b and a clearance groove 42c are formed on the bottom end side beyond the O-ring groove 42a. The secondary cap 45 is screwed to this screw portion 42b.

The secondary jar 41 has a housing portion 43 having substantially the same shape as the outer shape of the primary packaging case 30 in a sealed state. The housing portion 43 is excavated from the tip (mouth portion 42) of the secondary jar 41 to the vicinity of the middle in the longitudinal direction. The longitudinal length of the housing portion 43 is substantially equal to that of the primary packaging case 30 in a sealed state.

In the secondary jar 41, a gripping portion 44 is formed on the bottom end side beyond the housing portion 33. The gripping portion 34 has a cylindrical shape. This makes it easier to pinch the secondary jar 41 with fingers.

The secondary cap (secondary lid) 45 is a short bottomed cylindrical member and has a cylindrical portion 46 to be screwed into the secondary jar 41.

On the inner peripheral surface of the cylindrical portion 46, a screw portion 46a is formed. The screw portion 46a is screwed to the screw portion 42b of the secondary jar 41. Furthermore, on the inner peripheral surface of the cylindrical portion 46, a tapered hole portion 46b is formed on the bottom end side beyond the screw portion 42b. When the secondary cap 45 is screwed to the secondary jar 41, the tapered hole portion 46b is closely attached to the secondary O-ring 49.

In the secondary cap 45, a gripping portion 47 is also formed on the bottom end side of the cylindrical portion 46. The gripping portion 47 has a cylindrical shape, and three chamfers 47a are formed thereon. This makes it easier to pinch the secondary cap 45 with fingers.

[Manufacturing Method: Process A]

The fixture 10 and the packaging case 20 are respectively produced through the following process A.

[First Process A1: Forming Process]

Powder of zirconia (PXA-200 type manufactured by TOSOH CORPORATION, or the like) is put into a mold having a cavity of the same form as that of the fixture 10, and press molded. After that, the press-molded article is sintered at a temperature of, for example, 1500° C. or more.

As a result, a formed article of the fixture 10 is obtained.

In the same manner, the primary packaging case 30 is formed through press sintering treatment. When the abutment 8 and the implant crown 6 are formed of zirconia, they are similarly formed through press sintering treatment.

Separately, the secondary packaging case 40 is formed by cutting a raw material of PEEK.

[Second Process A2: γ-Ray Sterilization Treatment Process (Dark-Browning Process)]

First, the fixture 10 is housed in the packaging case 20. The fixture 10 is housed in the primary packaging case 30, and the primary packaging case 30 is housed in the secondary packaging case 40.

Next, the packaging case 20 housing the fixture 10 is sterilized (disinfected) by irradiation with a γ-ray. Irradiation is performed with the γ-ray in a dose of for example, 25 kGy (25 kSv) or more.

The γ-ray penetrates the secondary packaging case 40, the primary packaging case 30 and the fixture 10. As a result, the fixture 10 and the primary packaging case 30 turn dark brown. The fixture 10 and the primary packaging case 30 turn dark brown not only on the outside surface but also on the inside.

Note that there is no change such as discoloration on the appearance of the secondary packaging case 40.

[Third Process A3: Heat Treatment Process (Whitening Process)]

The packaging case 20 housing the fixture 10 is heated to 100° C. to 300° C. The highest temperature may be 100° C. to 300° C. The heating time, the retention time and the like can be set arbitrarily.

As a result, the dark-browned fixture 10 and primary packaging case 30 are whitened, and colored to a color approximate to that of a natural tooth. The fixture 10 and the primary packaging case 30 are colored to a color approximate to that of a natural tooth not only on the outside surface but also on the inside. That is, a prosthesis colored to a color approximate to that of a natural tooth (fixture 10) is obtained.

Verification Experiment 1

Table 1 is a table showing colorimetric results of the prostheses S1 to S13 formed through the above-described production process A (A1 to A3).

TABLE 1

|  |  | Brightness | Hue | | Chroma SQRT |
|---|---|---|---|---|---|
|  |  | L* (D65) | a* (D65) | b* (D65) | $(a^{*2} + b^{*2})$ |
| Test pieces | S1 | 65.61 | 5.48 | 2.52 | 6.03 |
|  | S2 | 75.23 | 2.39 | 5.88 | 6.35 |
|  | S3 | 77.47 | 1.73 | 6.37 | 6.60 |
|  | S4 | 80.29 | 0.63 | 6.61 | 6.64 |
|  | S5 | 81.25 | 0.32 | 6.29 | 6.30 |
|  | S6 | 81.60 | −0.10 | 6.16 | 6.16 |

TABLE 1-continued

|  |  | Brightness | Hue | | Chroma SQRT |
|---|---|---|---|---|---|
|  |  | L* (D65) | a* (D65) | b* (D65) | $(a^{*2} + b^{*2})$ |
|  | S7 | 83.10 | −0.43 | 5.98 | 6.00 |
|  | S8 | 83.35 | −0.62 | 5.83 | 5.86 |
|  | S9 | 84.18 | −1.06 | 5.08 | 5.19 |
|  | S10 | 84.58 | −1.32 | 4.36 | 4.56 |
|  | S11 | 84.98 | −1.56 | 3.71 | 4.02 |
|  | S12 | 88.22 | −1.48 | −0.04 | 1.48 |
|  | S13 | 87.94 | −1.37 | −0.08 | 1.37 |
| Comparison pieces | S21 | 86.88 | −1.25 | −0.74 | 1.45 |
|  | S22 | 45.32 | 6.07 | −0.17 | 6.07 |
|  | S23 | 63.99 | −1.11 | 7.77 | 7.85 |

Figure 7:
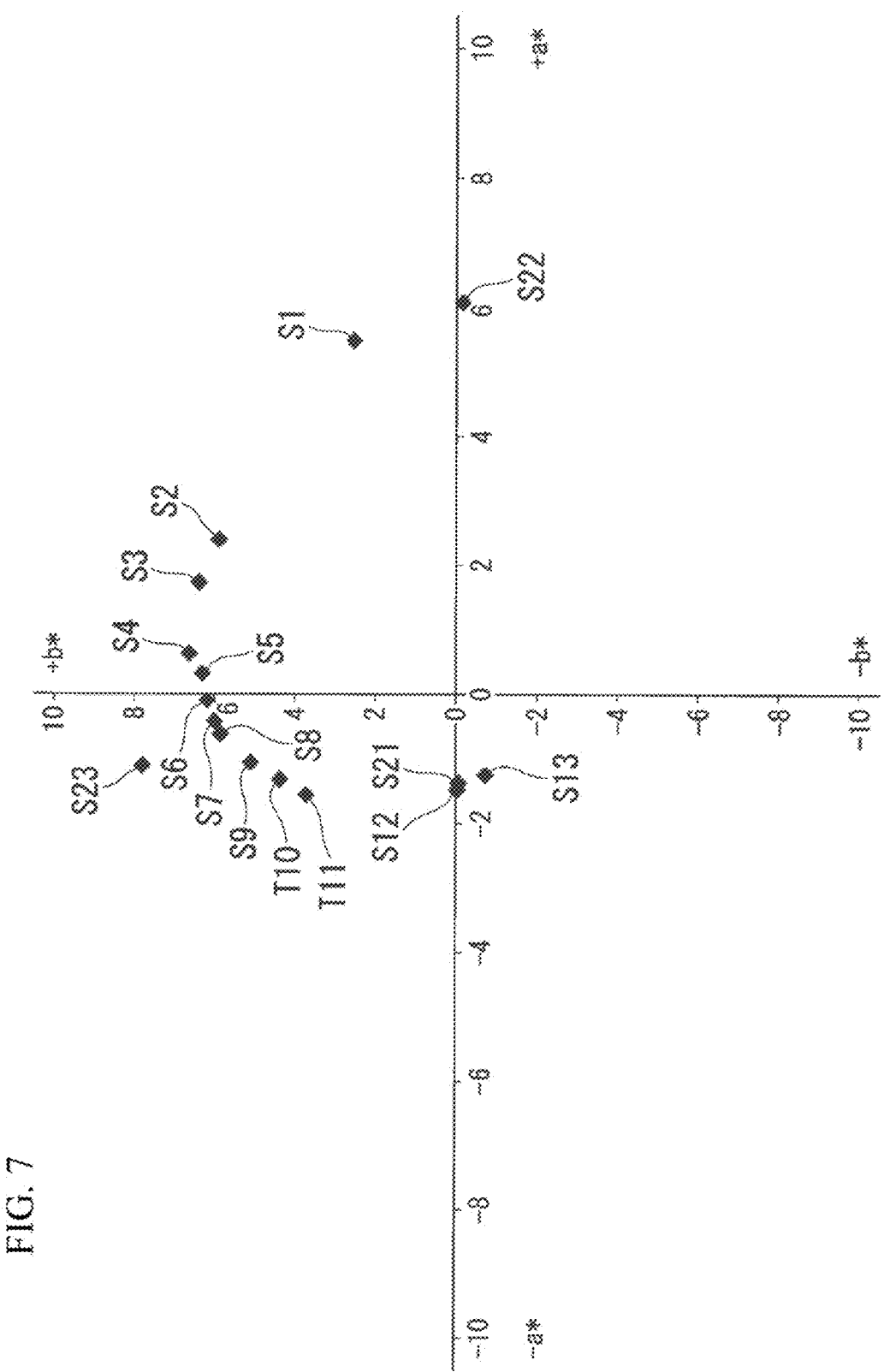
FIG. 7 is a chart showing colorimetric results (hue in the L*a*b* color space) of prostheses S1 to S13.

FIG. 7 is a chart showing colorimetric results (hue in the L*a*b* color space) of prostheses S1 to S13.

Figure 8:
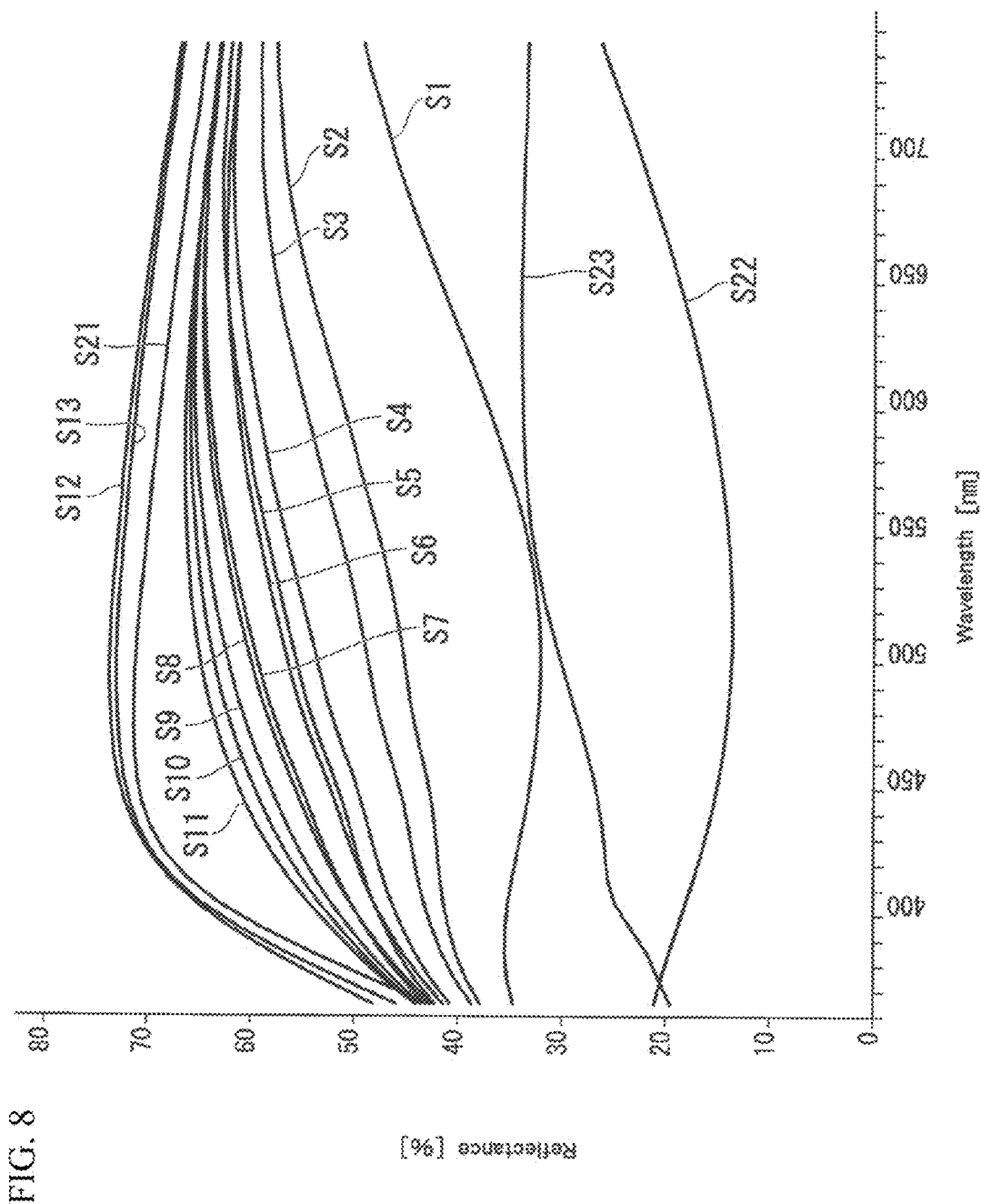
FIG. 8 is a chart showing colorimetric results (wavelength and reflectivity) of prostheses S1 to S13.

FIG. 8 is a chart showing colorimetric results (wavelength and reflectivity) of prostheses S1 to S13.

Figure 9:
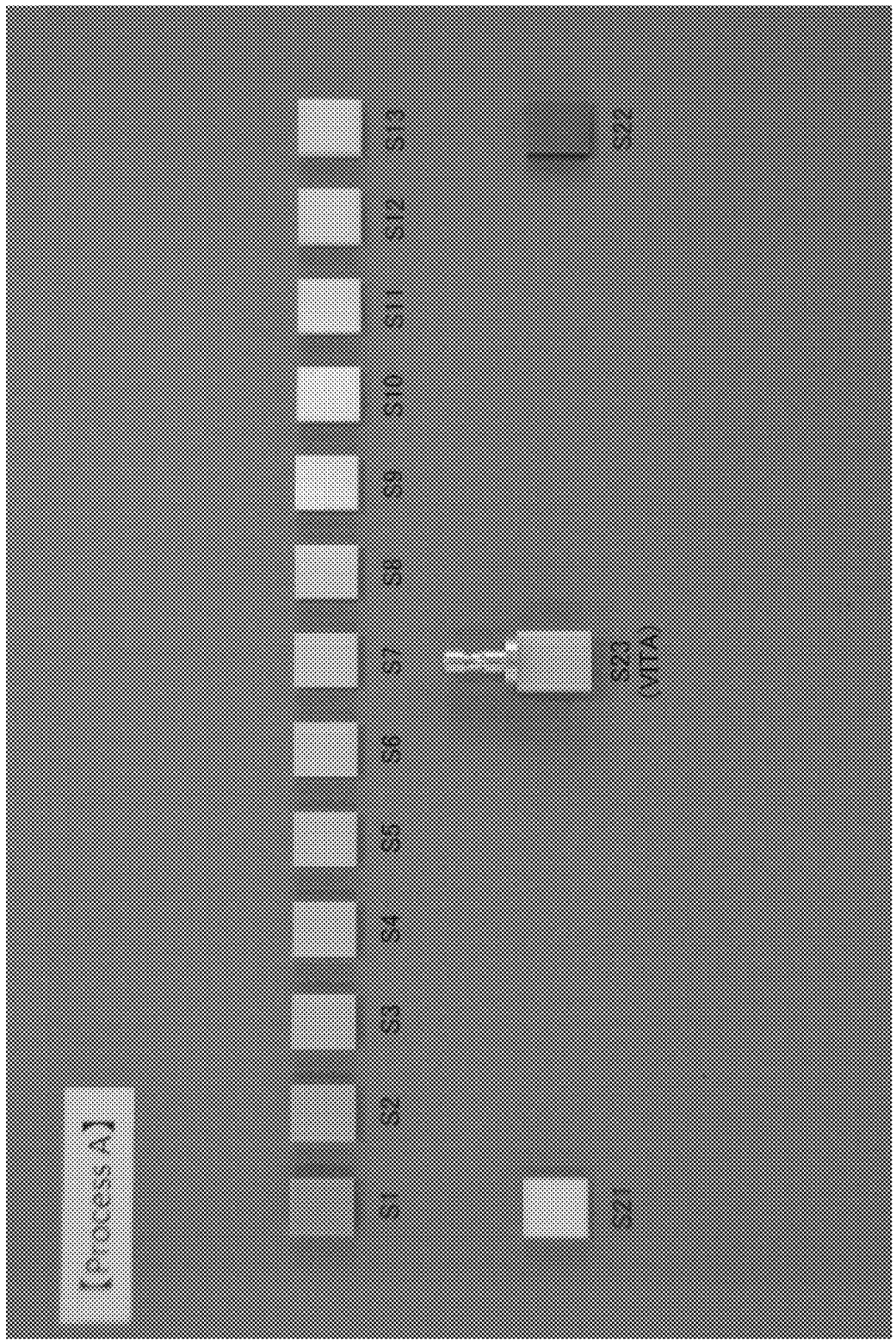
FIG. 9 is a diagram showing prostheses S1 to S13.

FIG. 9 is a diagram showing prostheses S1 to S13.

Color system: Lab color system (CIE 1976 (L*, a*, and b*) color space (CIELAB), JIS Z 8729)

Spectrophotometer: CM-1000 manufactured by KONICA MINOLTA, INC. (former Minolta Camera Co., Ltd.)

Materials of prostheses S1 to S13, and comparative examples S21 and S22: PXA-233P manufactured by TOSOH CORPORATION Prosthesis S1: the highest temperature is set to 100° C. in the third process A3.

Prosthesis S2: the highest temperature is set to 110° C. in the third process A3.

Prosthesis S3: the highest temperature is set to 120° C. in the third process A3.

Prosthesis S4: the highest temperature is set to 130° C. in the third process A3.

Prosthesis S5: the highest temperature is set to 140° C. in the third process A3.

Prosthesis S6: the highest temperature is set to 150° C. in the third process A3.

Prosthesis S7: the highest temperature is set to 160° C. in the third process A3.

Prosthesis S8: the highest temperature is set to 170° C. in the third process A3.

Prosthesis S9: the highest temperature is set to 180° C. in the third process A3.

Prosthesis S10: the highest temperature is set to 190° C. in the third process A3.

Prosthesis S11: the highest temperature is set to 200° C. in the third process A3.

Prosthesis S12: the highest temperature is set to 250° C. in the third process A3.

Prosthesis S13: the highest temperature is set to 300° C. in the third process A3.

Comparative example S21: subjected to the first process A1 (the second process A2 and the third process A3 being omitted).

Comparative example S22: subjected to the first process A1 and the second process A2 (the third process A3 being omitted).

Comparative example S23: a conventional artificial tooth (CEREC VITABLOCS MarkII manufactured by VITA).

The prostheses S1 to S13 are changed to a color approximate to that of the natural bone by the heat treatment (the third process A3) after the γ-ray sterilization treatment (the second process A2). The highest temperature in the heat treatment (the third process A3) is 100° C. to 300° C.

As shown in FIG. 7, the color approximate to that of the natural bone has an L* value of 60 to 90, an a* value of −5 to 10, and a b* value of −5 to 10 in the L*a*b* color space. Specifically, the L* value is 65 to 89, the a* value is −2 to 6, and the b* value is −1 to 8.

Prostheses S1 to S13 are whiter than the comparative example S22 that is dark brown, and browner than the comparative example S21 that is pure white. Therefore, the prostheses S1 to S13 are changed to a color approximate to that of the natural bone in the same manner as in the comparative example S23.

As shown in FIG. 8, prostheses S1 to S13 have higher reflectivity than that of the comparative example S23, but have a waveform shape approximate to that of the comparative example S23. Prostheses S1 to S13 have a waveform shape approximate to that of the comparative example S23, and are therefore recognized to have been changed to a color approximate to that of the comparative example S23 (color approximate to that of the natural bone).

As shown in FIG. 9, it was confirmed that prostheses S1 to S13 were colored to a color approximate to that of the natural bone (the same color as that of the comparative example S23). In particular, by setting the highest temperature in the heat treatment (the third process A3) to 100° C. to 300° C., prostheses S1 to S13 having a color approximate to that of the natural tooth of a patient (wearer) were obtained.

[Manufacturing Method: Process B]

The fixture 10 and the packaging case 20 can also be produced through the following process B.

[First Process B1: Forming Process]

The fixture 10 and the primary packaging case 30 are formed through press sintering treatment. The secondary packaging case 40 is formed by cutting a raw material of PEEK.

The first process B1 is the same process as that of the first process A1.

[Second Process B2: Surface Treatment Process (Laser Processing Process)]

The surface of the fixture 10 is roughened by irradiation with a laser beam.

As the laser beam, a Nd: YAG laser or YVO4 laser is used. For example, a fundamental wave of a Nd: YAG laser or YVO4 laser (solid-state laser: wavelength 1064 nm, and fiber laser: 1090 nm) can be used. The beam diameter (diameter) of the laser beam is, for example, 5 to 50 μm.

By the irradiation with a laser beam, the fixture 10 discolors (turns into dark brown).

[Third Process B3: High Temperature Heat Treatment Process (Color Restoration Process)]

The fixture 10 is heated to 700° C. The heating time, the retention time, and the like can be set arbitrarily.

As a result, the discolored (dark-browned) fixture 10 is whitened by the irradiation with a laser beam. The fixture 10 is whitened not only on the outside surface but also on the inside.

[Fourth Process B4: γ-Ray Sterilization Treatment Process (Dark-Browning Process)]

The fixture 10 and the packaging case 20 are disinfected by irradiation with a γ-ray.

The fourth process B4 is the same process as that of the second process A2.

[Fifth Process B5: Heat Treatment Process (Whitening Process)]

The packaging case 20 housing the fixture 10 is heated to 100° C. to 300° C. The fifth process B5 is the same process as that of the third process A3.

Verification Experiment 2

Table 2 is a table showing colorimetric results of the prostheses T1 to T13 formed through the above-described production process B (B1 to B5).

TABLE 2

|  |  | Brightness | Hue | | Chroma SQRT |
|---|---|---|---|---|---|
|  |  | L* (D65) | a* (D65) | b* (D65) | $(a^{*2} + b^{*2})$ |
| Test pieces | T1 | 74.15 | 2.71 | 0.03 | 2.71 |
|  | T2 | 80.81 | 1.28 | 3.24 | 3.48 |
|  | T3 | 83.92 | −0.37 | 4.18 | 4.20 |
|  | T4 | 84.99 | −0.90 | 4.45 | 4.54 |
|  | T5 | 85.75 | −1.01 | 4.61 | 4.72 |
|  | T6 | 85.86 | −1.29 | 4.14 | 4.34 |
|  | T7 | 86.36 | −1.37 | 3.89 | 4.12 |
|  | T8 | 87.19 | −1.62 | 4.10 | 4.41 |
|  | T9 | 86.71 | −1.71 | 3.31 | 3.73 |
|  | T10 | 87.51 | −1.74 | 3.23 | 3.67 |
|  | T11 | 88.13 | −1.75 | 2.61 | 3.14 |
|  | T12 | 88.07 | −1.25 | −0.41 | 1.32 |
|  | T13 | 88.04 | −1.12 | −0.08 | 1.12 |
| Comparison pieces | T21 | 68.70 | 3.30 | 3.14 | 4.56 |
|  | T22 | 87.92 | −1.20 | −0.42 | 1.27 |
|  | T23 | 66.04 | 1.88 | −1.94 | 2.70 |
|  | T24 | 63.99 | −1.11 | 7.77 | 7.85 |

Figure 10:
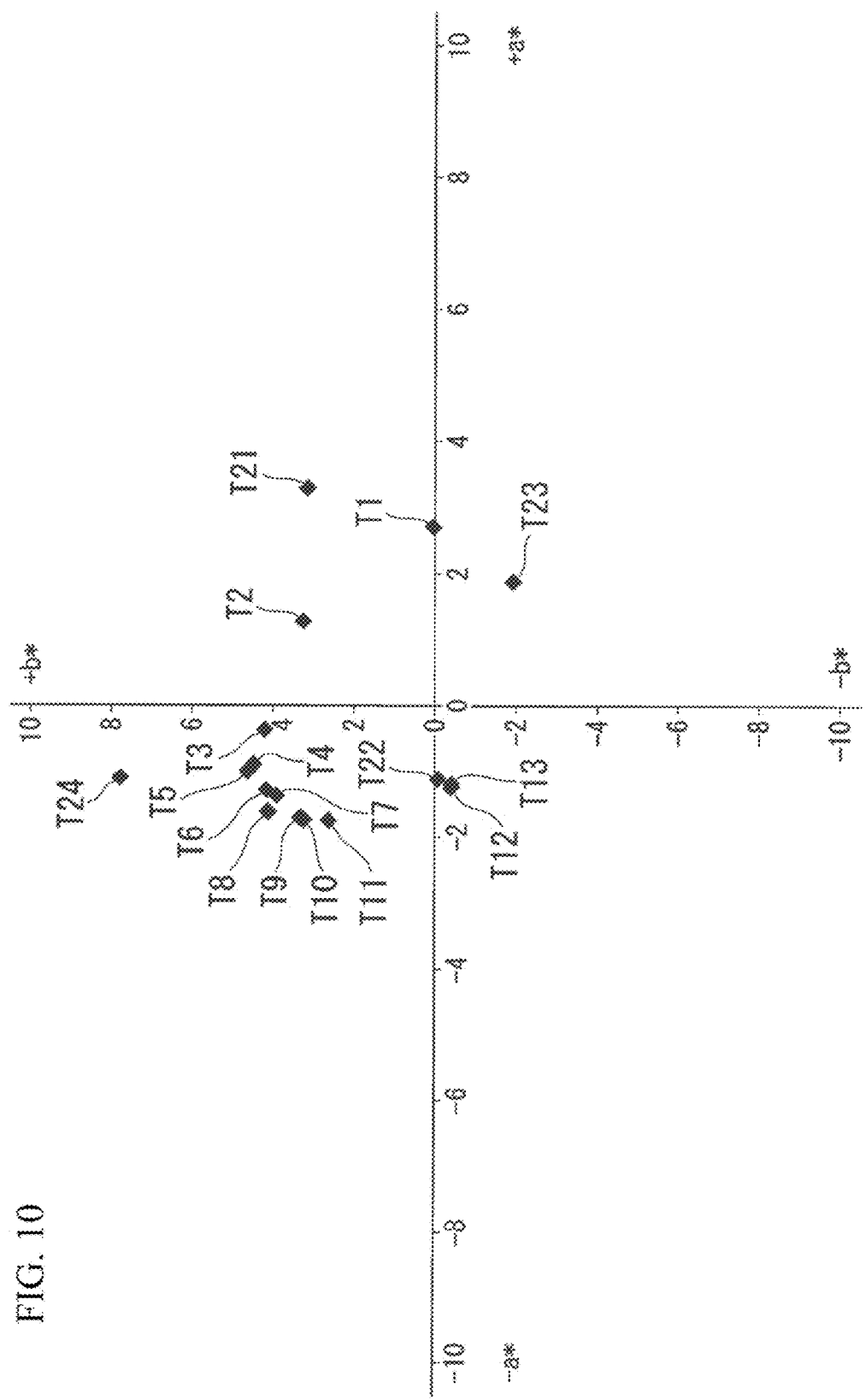
FIG. 10 is a chart showing colorimetric results (hue in the L*a*b* color space) of prostheses T1 to T13.

FIG. 10 is a chart showing colorimetric results (hue in the L*a*b* color space) of prostheses T1 to T13.

Figure 11:
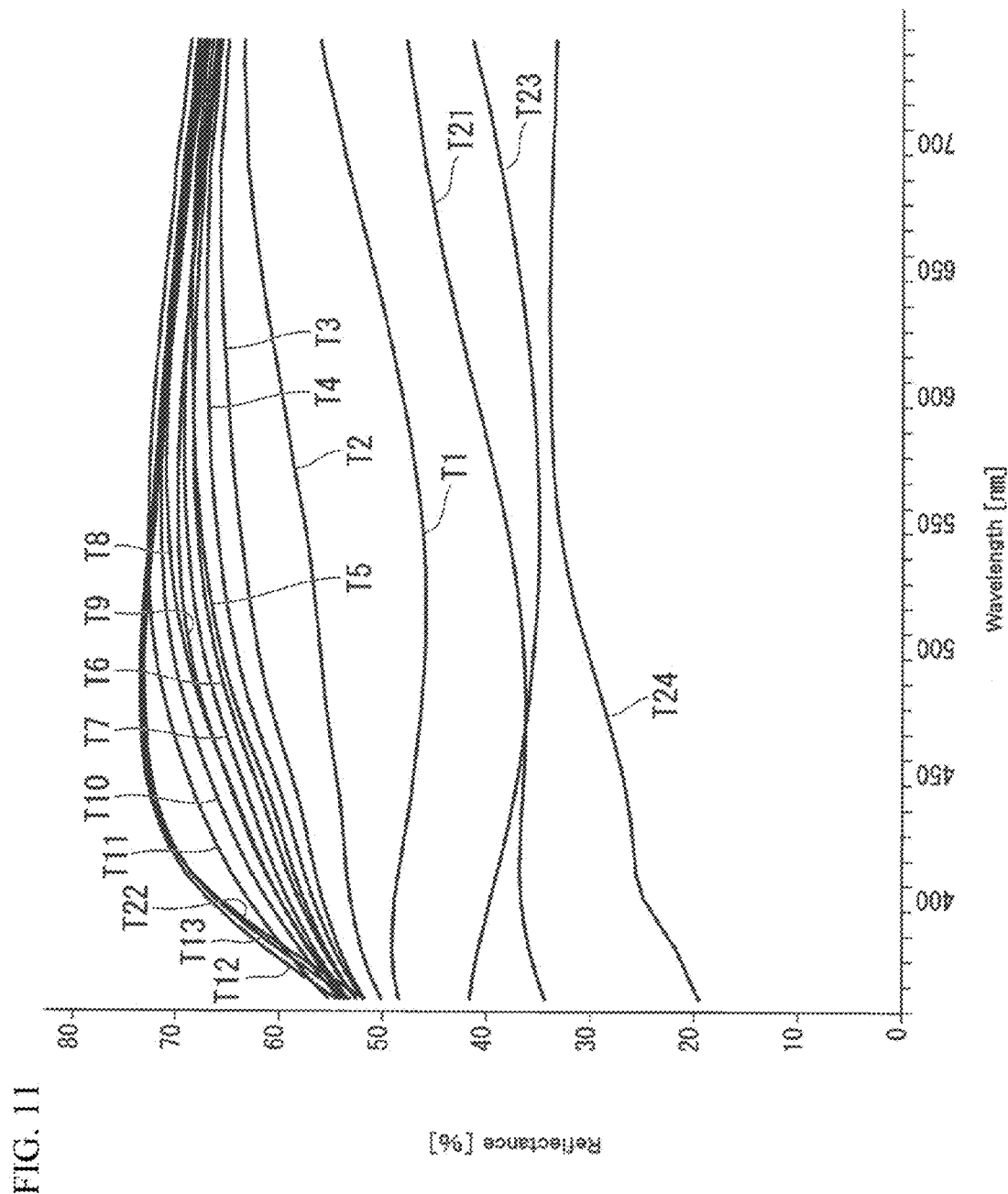
FIG. 11 is a chart showing colorimetric results (wavelength and reflectivity) of prostheses T1 to T13.

FIG. 11 is a chart showing colorimetric results (wavelength and reflectivity) of prostheses T1 to T13.

Figure 12:
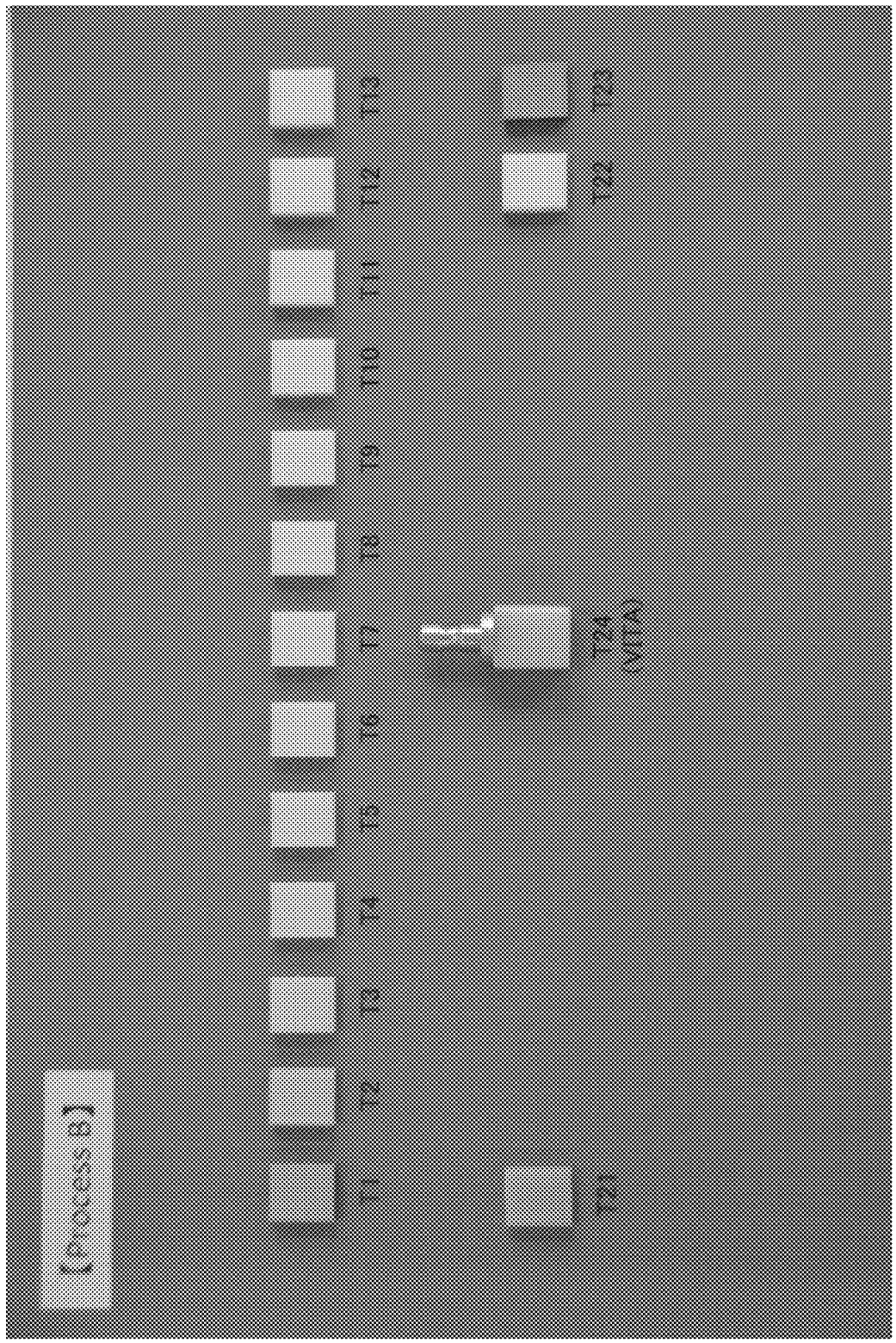
FIG. 12 is a diagram showing prostheses T1 to T13.

FIG. 12 is a diagram showing prostheses S1 to S13.

Color system: Lab color system (CIE 1976 (L*, a*, and b*) color space (CIELAB), JIS Z 8729)

Spectrophotometer: CM-1000 manufactured by KONICA MINOLTA, INC. (former Minolta Camera Co., Ltd.)

Materials of prostheses T1 to T13, and comparative examples T21 to T23: PXA-233P manufactured by TOSOH CORPORATION Prosthesis T1: the highest temperature is set to 100° C. in the fifth process B5.
Prosthesis T2: the highest temperature is set to 110° C. in the fifth process B5.
Prosthesis T3: the highest temperature is set to 120° C. in the fifth process B5.
Prosthesis T4: the highest temperature is set to 130° C. in the fifth process B5.
Prosthesis T5: the highest temperature is set to 140° C. in the fifth process B5.
Prosthesis T6: the highest temperature is set to 150° C. in the fifth process B5.
Prosthesis T7: the highest temperature is set to 160° C. in the fifth process B5.
Prosthesis T8: the highest temperature is set to 170° C. in the fifth process B5.
Prosthesis T9: the highest temperature is set to 180° C. in the fifth process B5.
Prosthesis T10: the highest temperature is set to 190° C. in the fifth process B5.
Prosthesis T11: the highest temperature is set to 200° C. in the fifth process B5.
Prosthesis T12: the highest temperature is set to 250° C. in the fifth process B5.
Prosthesis T13: the highest temperature is set to 300° C. in the fifth process B5.

Comparative example T21: subjected to the first process B1 and the second process B2 (the third process B3 to the fifth process B5 being omitted).

Comparative example T22: subjected to the first process B1 to the third process B3 (the fourth process B4 and the fifth process B5 being omitted).

Comparative example T23: subjected to the first process B1 to the fourth process B4 (the fifth process B5 being omitted).

Comparative example T24: a conventional artificial tooth (CEREC VITABLOCS MarkII manufactured by VITA). The comparative example T24 is the same as the comparative example S23.

The prostheses T1 to T13 are changed to a color approximate to that of the natural bone by the heat treatment (the fifth process B5) after the γ-ray sterilization treatment (the fourth process B4). The highest temperature in the heat treatment (the fifth process B5) is 100° C. to 300° C.

As shown in FIG. 10, the color approximate to that of the natural bone has an L* value of 60 to 90, an a* value of −5 to 10, and a b* value of −5 to 10 in the L*a*b* color space. Specifically, the L* value is 65 to 89, the a* value is −2 to 6, and the b* value is −1 to 8.

Prostheses T1 to T13 are whiter than the comparative examples T21 and T23 that are dark brown, and browner than the comparative example T22 that is pure white. Therefore, the prostheses S1 to S13 are changed to a color approximate to that of the natural bone in the same manner as in the comparative example T24.

As shown in FIG. 11, the prostheses T1 to T13 have higher reflectivity than that of the comparative example T24, but have a waveform shape approximate to that of the comparative example T24. The prostheses T1 to T13 have a waveform shape approximate to that of the comparative example T24, and are therefore recognized to have been changed to a color approximate to that of the comparative example T24 (color approximate to that of the natural bone).

As shown in FIG. 12, it was confirmed that prostheses T1 to T13 are colored to a color approximate to that of the natural bone (the same color as that of the comparative example T24). In particular, by setting the highest temperature in the heat treatment (the fifth process B5) to 100° C. to 300° C., prostheses T1 to T13 having color approximate to that of the natural tooth of a patient (wearer) were obtained.

[Effects of the Packaging Case 20]

As described above, the packaging case 20 can be subjected to the γ-ray sterilization treatment and the heat treatment while housing the zirconia fixture 10. In addition, the sterilized state of the fixture 10 colored to a color approximate to that of a natural bone can be maintained for a long period.

Since the primary packaging case 30 is made of the same material as of the fixture 10, foreign matters do not adhere to the fixture 10 (non dust-generating property). In particular, since the primary packaging case 30 is made of ceramics containing zirconia, the risk of metal allergy can be avoided.

Furthermore, the primary packaging case 30 does not change its nature even when subjected to the γ-ray sterilization treatment and the heat treatment (radiation resistance, heat resistance), and can house the fixture 10 for a long period (durability, stability).

In addition, in the primary packaging case 30, the primary jar 31 and the primary cap 35 are fitted and connected to each other. Thereby, difficulty of unsealing due to burning of the primary jar 31 and the primary cap 35 can be eliminated. That is, the primary packaging case 30 made of zirconia can be smoothly sealed and unsealed.

In the secondary packaging case 40, the secondary jar 41 and the secondary cap 45 are screwed and connected to each other, and also the primary packaging case 30 is housed with no gap. Thereby, the secondary packaging case 40 can prevent the primary packaging case 30 from opening during the heat treatment.

Furthermore, the secondary packaging case 40 does not change its nature even when subjected to the γ-ray sterilization treatment and the heat treatment (radiation resistance, heat resistance), and can house the fixture 10 for a long period (durability, stability).

The packaging case 20 may house the abutment 8 and the implant crown 6 which are colored to a color approximate to that of a natural bone.

[Effects of the Fixture 10]

The fixture 10 is colored to a color approximate to that of a natural bone. In addition, since the coloring material is not used in the fixture 10, there is no adverse effect on the human body. Similarly, the abutment 8 and the implant crown 6 can also be colored to a color approximate to that of a natural bone. Thereby, aesthetics in the oral cavity is not compromised.

Also, the packaging case 20 is colored to a color approximate to that of a natural bone (the same color as of the fixture 10).

The fixture 10 is subjected to the γ-ray sterilization treatment and the heat treatment while housed in the packaging case 20. Then, it is stored and transported as it is. Hence, the sterilized state can be maintained in the fixture 10 for a long period.

In particular, since the primary packaging case 30 is made of the same material as of the fixture 10, foreign matters do not adhere to the fixture 10. Since no metal adheres to the fixture 10, the risk of metal allergy can be avoided.

[Artificial Joint Implant 70]

Figure 13:
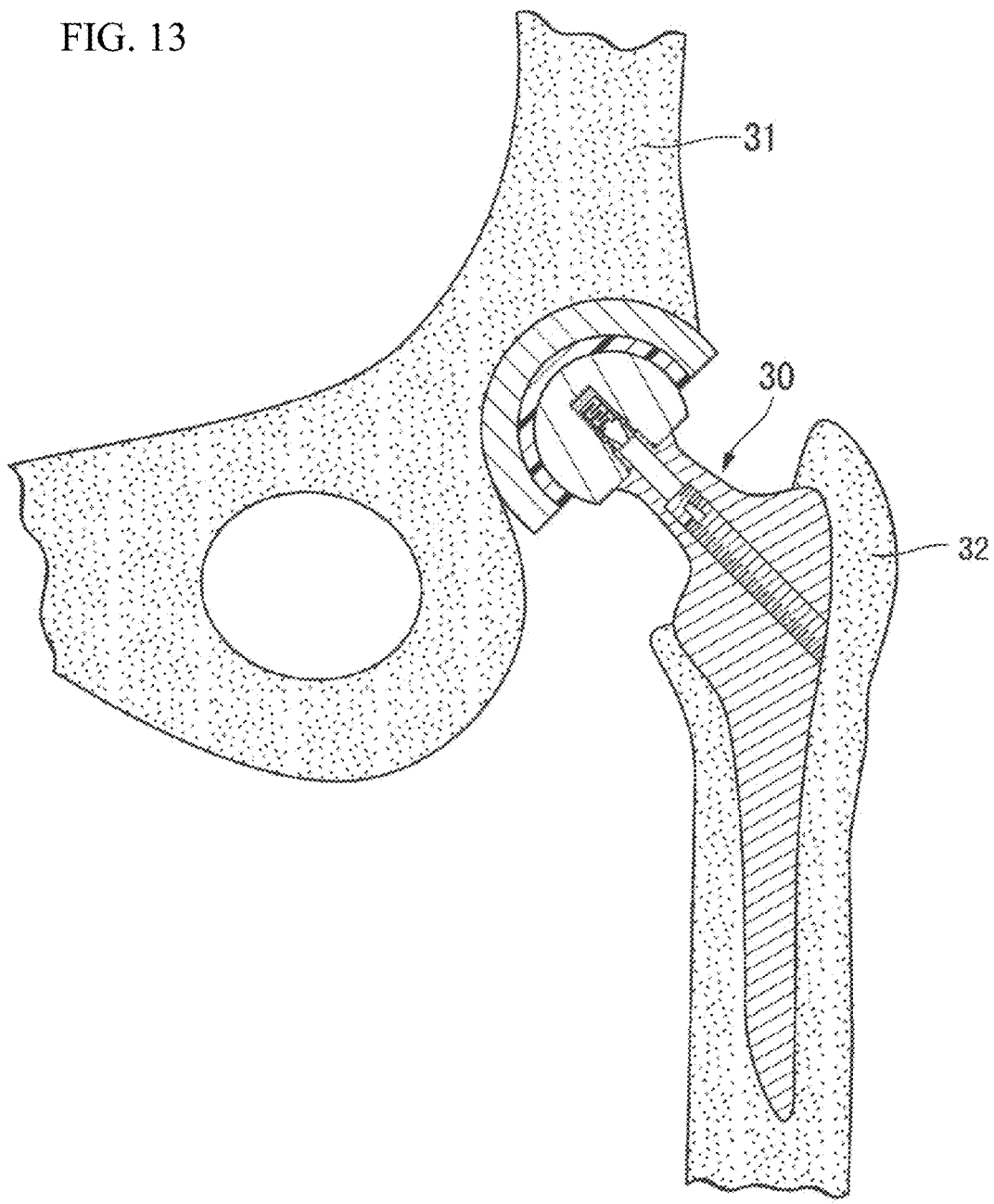
FIG. 13 is a diagram showing an artificial joint implant 70 according to the embodiment of the present invention.

FIG. 13 illustrates a view showing an artificial joint implant 70 according to the embodiment of the invention.

The prosthesis of the present invention may be the artificial joint implant 70.

The artificial joint implant 70 is formed of ceramics containing zirconia. The artificial joint implant 70 may be partially formed of zirconia.

An artificial joint implant (prosthesis, implant, prosthesis with packaging case) 70 is embedded in a pelvis 71 and a femur 72 of a hip joint.

The heat treatment (the third process A3, or the fifth process B5) is also performed in the production process of the artificial joint implant 70, after the γ-ray sterilization treatment (the second process A2, or the fourth process B4).

Figure 14:
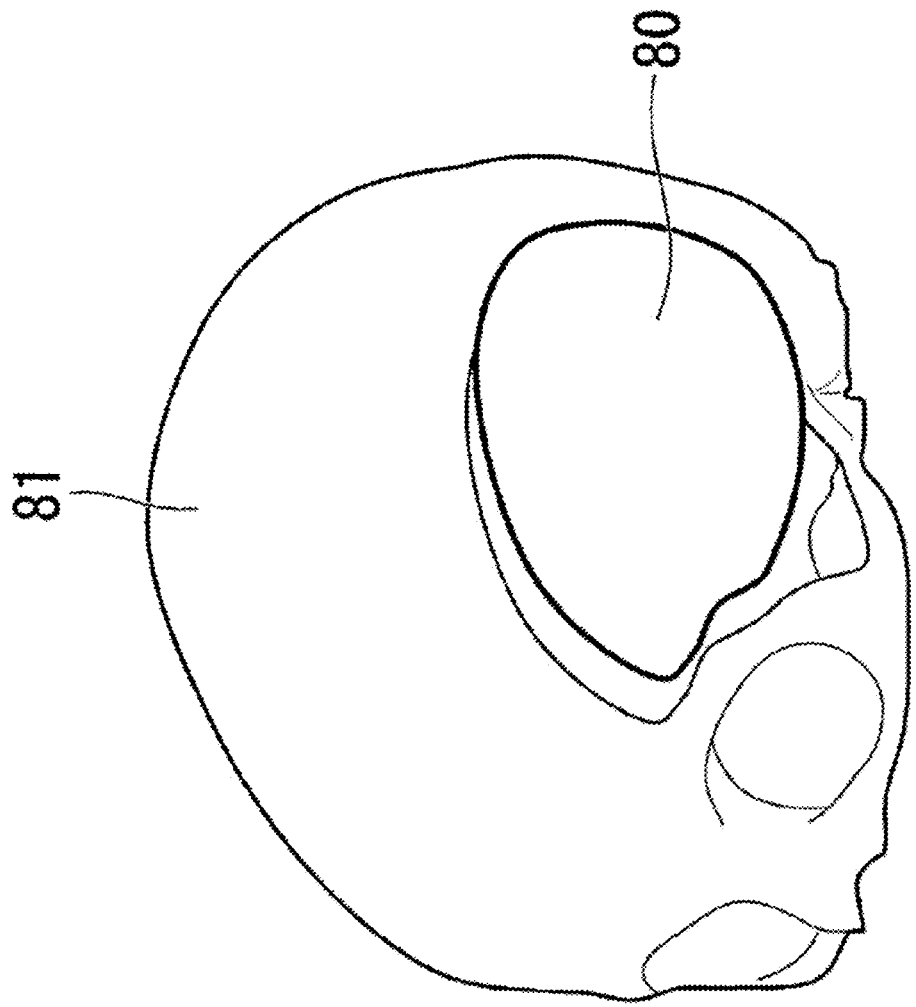
FIG. 14 is a diagram showing an artificial bone 80 according to the embodiment of the present invention.

FIG. 14 is a diagram showing an artificial bone 80 according to the embodiment of the present invention.

The prosthesis of the present invention may be an artificial bone 80.

The artificial bone (prosthesis, implant, prosthesis with packaging case) 80 is a skull plate that is arranged on a defective portion of a skull 81.

The artificial bone 80 is formed of ceramics containing zirconia. The artificial bone 80 may be partially formed of zirconia.

The heat treatment (the third process A3, or the fifth process B5) is also performed in the production process of an artificial bone 80, after the γ-ray sterilization treatment (the second process A2, or the fourth process B4).

[Effects of Artificial Joint Implant 70 and Artificial Bone 80]

The artificial joint implant 70 and the artificial bone 80 are colored to a color approximate to that of the natural bone without using a coloring material. Therefore, the aesthetics is not compromised. In addition, a colored material is not used; therefore, there is no adverse effect on the human body.

The artificial joint implant 70 and an artificial bone 80 are double-packaged in a packaging case (not shown) having the same configuration as of the packaging case 20. This packaging case has a housing portion having substantially the same shape as the outer shape of the artificial joint implant 70 and the artificial bone 80.

Therefore, the packaging case is subjected to the γ-ray sterilization treatment and the heat treatment while housing the artificial joint implant 70 and the like. Consequently, in the artificial joint implant 70 and the like colored to a color approximate to that of a natural bone, the sterilized state can be maintained for a long period.

[Other Configuration Included in the Present Invention]

The technical scope of the present invention should not be limited to the above-described embodiments. Without departing from the gist of the present invention, the present invention also includes ones in which various changes have been added to the above-described embodiments. The specific materials, layer composition, and the like which have been mentioned in the embodiments are only examples, and can be changed appropriately.

The prosthesis and the prosthesis-packaging case (the prosthesis with the packaging case) of the present invention is formed of a biocompatible ceramic material containing zirconia (zirconium oxide) as a main component. The prosthesis and the prosthesis-packaging case of the present invention may contain zirconia at the volume ratio of 50% or more.

The material of the prosthesis and the prosthesis-packaging case (the prosthesis with the packaging case) of the present invention may be a zirconia composite material (a combination of zirconia and other ceramic materials). Examples of the other ceramic materials include alumina (aluminum oxide), yttrium oxide, hafnium oxide, silicon oxide, magnesium oxide, and cerium oxide.

The material of the prosthesis and the prosthesis-packaging case (the prosthesis with the packaging case) of the present invention may be a combination of zirconia and a metal or alloy. Examples of the metal or alloy include copper, titanium, and a titanium alloy.

The material of the prosthesis and the prosthesis-packaging case (the prosthesis with the packaging case) of the present invention may be a combination of zirconia, carbon, resin, glass, or the like.

The heat treatment (the third process A3, or the fifth process B5) is performed in the production process of the prosthesis and the prosthesis-packaging case (the prosthesis with the packaging case) of the present invention, after the γ-ray sterilization treatment (the second process A2, or the fourth process B4).

In the forming process (the first processes A1, or B1), an arbitrary production method and an arbitrary apparatus can be used.

In the surface treatment process (the second process B2) and the high temperature heat treatment process (the third process B3), an arbitrary production method and an arbitrary apparatus can be used.

The artificial joint implant of the present invention may be embedded not only in a hip joint but also in a shoulder joint, a knee joint, an elbow joint, a wrist, an ankle, a jaw joint and the like.

The artificial bone of the present invention may be used not only to be placed in a deficient part of a bone but also to fix a broken bone. The artificial bone may be in a form of e.g. a wood screw, a bolt, a nail, a stud, a beam or the like.

The prosthesis may be of a type with a particular shape like an artificial bone but also of a type without a particular shape like a bone prosthetic material (not shown).

The prosthesis of the present invention is not limited to one fixed to bone. It may be any prosthesis embedded in a body, or any prosthesis placed on the surface of the body and partly embedded in the body.

The fixture 10 may be one without a threading function (self tap 13) (normal type). The rotation stopper 33a need not be provided on the housing portion 33 of the primary jar 31.

The invention claimed is:

1. A prosthesis-packaging case used in subjecting a prosthesis made of a material containing zirconia to γ-ray sterilization treatment and heat treatment while the prosthesis is double-packaged, comprising:
    a primary packaging case for housing the prosthesis, having a primary case body and a primary lid fitted to the primary case body; and
    a secondary packaging case for housing the primary package case with no gap in an opening direction of the primary package case, having a secondary case body and a secondary lid screwed to the secondary case body,
    wherein the primary packaging case comprises zirconia, and
    wherein the secondary packaging case is made of a thermoplastic resin.

2. The prosthesis-packaging case according to claim 1, wherein in the γ-ray sterilization treatment, irradiation is performed with a γ-ray in a dose of 25 kSv or more.

3. The prosthesis-packaging case according to claim 2, wherein the thermoplastic resin of the secondary packaging case is not damaged by heat treatment temperature having a highest temperature of 100° C. to 300° C.

4. The prosthesis-packaging case according to claim 2, wherein the prosthesis is an implant embedded in a body.

5. The prosthesis-packaging case according to claim 1, wherein the thermoplastic resin of the secondary packaging case is not damaged by heat treatment temperature having a highest temperature of 100° C. to 300° C.

6. The prosthesis-packaging case according to claim 5, wherein the prosthesis is an implant embedded in a body.

7. The prosthesis-packaging case according to claim 1, wherein the prosthesis is an implant embedded in a body.

8. The prosthesis-packaging case according to claim 7, wherein the prosthesis is a dental implant.

9. The prosthesis-packaging case according to claim 7, wherein the prosthesis is an artificial joint implant.

10. The prosthesis-packaging case according to claim 7, wherein the prosthesis is an artificial bone or a bone prosthetic material.

11. The prosthesis-packaging case according to claim 1, wherein the thermoplastic resin of the secondary packaging case is not damaged by heat treatment at 200° C.

12. The prosthesis-packaging case according to claim 1, wherein the thermoplastic resin of the secondary packaging case is polyether ether ketone.

13. A method of preparing a prosthesis, comprising:
    inserting a prosthesis into a primary packaging case, the prosthesis and the primary packaging case both comprising zirconia,
    inserting a combination of the primary packaging case and the prosthesis into a secondary packaging case, the secondary packaging case comprising a thermoplastic resin,
    irradiating a combination of the prosthesis, the primary packaging case, and the secondary packaging case with a γ-ray, and
    heat treating the combination of the prosthesis, the primary packaging case, and the secondary packaging case to 100° C. to 300° C.

14. The method according to claim 13, wherein the irradiating step comprises irradiation with a γ-ray dose of 25 KGy or more.

15. The method according to claim 13, wherein the heat treating step comprises heating to 200° C.

* * * * *